(12) United States Patent
Zheng et al.

(10) Patent No.: US 10,557,043 B2
(45) Date of Patent: Feb. 11, 2020

(54) TEMPERATURE-SENSITIVE NANO SILVER CONTROLLED-RELEASE SMART ANTIBACTERIAL COATING AND PREPARATION METHOD THEREFOR

(71) Applicant: FU ZHOU UNIVERSITY, Fuzhou, Fujian (CN)

(72) Inventors: Yuying Zheng, Fujian (CN); Liangen Huang, Fujian (CN)

(73) Assignee: FU ZHOU UNIVERSIT, Fuzhou, Fujian (CN)

( * ) Notice: Subject to any disclaimer, the term of this patent is extended or adjusted under 35 U.S.C. 154(b) by 0 days.

(21) Appl. No.: 16/073,779

(22) PCT Filed: Jan. 15, 2018

(86) PCT No.: PCT/CN2018/072546
§ 371 (c)(1),
(2) Date: Jul. 28, 2018

(87) PCT Pub. No.: WO2018/133750
PCT Pub. Date: Jul. 26, 2018

(65) Prior Publication Data
US 2019/0031891 A1 Jan. 31, 2019

(30) Foreign Application Priority Data
Jan. 18, 2017 (CN) .......................... 2017 1 0032815

(51) Int. Cl.
| | |
|---|---|
| *C09D 5/14* | (2006.01) |
| *C09D 133/00* | (2006.01) |
| *C08L 33/08* | (2006.01) |
| *C09D 7/65* | (2018.01) |
| *C09D 7/45* | (2018.01) |
| *C09D 7/47* | (2018.01) |
| *A01N 25/10* | (2006.01) |
| *A01N 59/16* | (2006.01) |
| *C09D 5/26* | (2006.01) |
| *C09D 133/04* | (2006.01) |

(52) U.S. Cl.
CPC .............. *C09D 5/14* (2013.01); *A01N 25/10* (2013.01); *A01N 59/16* (2013.01); *C08L 33/08* (2013.01); *C09D 5/26* (2013.01); *C09D 7/45* (2018.01); *C09D 7/47* (2018.01); *C09D 7/65* (2018.01); *C09D 133/00* (2013.01); *C09D 133/04* (2013.01); *C08K 2201/011* (2013.01); *C08L 2205/035* (2013.01)

(58) Field of Classification Search
CPC .......... C08L 33/08; C08L 75/04; C08L 75/00; C08K 3/10; C08K 5/0008; C08K 2201/011; A01N 25/10; A01N 59/16; C09D 133/04; C09D 133/00; C09D 5/14; C09D 5/26; C09D 7/45; C09D 7/47; C09D 7/65
See application file for complete search history.

(56) References Cited

U.S. PATENT DOCUMENTS

| | | | |
|---|---|---|---|
| 5,064,576 A | 11/1991 | Suto | |
| 2015/0147372 A1* | 5/2015 | Agrawal | ................. A61L 15/46 424/405 |
| 2016/0251571 A1* | 9/2016 | Agrawal | ................ A61K 33/18 507/219 |

FOREIGN PATENT DOCUMENTS

| | | |
|---|---|---|
| CN | 1730581 A | 2/2006 |
| CN | 102702889 A | 10/2012 |
| CN | 105238103 A | 1/2016 |
| CN | 106214644 A | 12/2016 |
| CN | 106752543 A | 5/2017 |

\* cited by examiner

*Primary Examiner* — Mark V Stevens
(74) *Attorney, Agent, or Firm* — Luoh J. Wu; Continent Patent Office LLP

(57) ABSTRACT

This present invention discloses a temperature-sensitive nano-silver controlled release antibacterial coating composite, which is comprises: water, acrylic, polyurethane resin, temperature-sensitive nano-silver controlled release antibacterial agent, dispersant, curing agent, defoamer, filming additive and leveling agent. By adsorbing nano silver particles into the pores of mesoporous $SiO_2$ modified by poly N-isopropyl acrylamide, we successfully prepared a temperature-sensitive nano-silver controlled release antibacterial agent. By adding the prepared agent to the conventional coating composite, we achieved "on-off" control of the antibacterial properties of coating composite. Through the control of temperature, the release of nano-silver in the mesoporous nano-silica of the coating film layer is controlled. This control method is not only to protect the nano-silver, but also to adjust the strength of the antibacterial properties according to the actual demands and improve the use-efficiency of nano silver particles. This invention is in line with the new concept of "Intelligent Age" in the 21st century.

6 Claims, 1 Drawing Sheet

TEMPERATURE-SENSITIVE NANO SILVER CONTROLLED-RELEASE SMART ANTIBACTERIAL COATING AND PREPARATION METHOD THEREFOR

CROSS-REFERENCE RELATED APPLICATIONS

This application is the national phase entry of International Application No. PCT/CN2018/072546, filed on Jan. 15, 2018, which is based upon and claims priority to Chinese Application No. CN 201710032815.1, filed on Jan. 18, 2017, the entire contents of which are incorporated herein by reference.

FIELD AND BACKGROUND OF THE INVENTION

This present invention, wherein a temperature-sensitive nano-silver controlled release antibacterial coating composite and a preparation method thereof are disclosed, belongs to the field of chemical coating.

Coating has a long history of development. Over 3,000 years ago, ancient Chinese people could use natural oils and resins such as tung oil and rosin to make coating. Since the eighteenth century, the development of modern natural sciences and the establishment of organic chemistry have laid a solid theoretical foundation for the study of coatings, and coatings have officially reached the industrial stage. From the 19th to the 20th century, with the establishment and development of polymer chemistry, coatings began to move toward the synthetic resin era. Epoxy, amino, nitro, polyester, polyurethane, acrylic, organic silicon, fluorocarbons functional coatings, etc. have emerged one after another. At the end of the 20th century, with the enhancement of people's awareness of environmental protection, coatings have developed in the direction of energy saving, resource conservation, and pollution-free. High-solid coatings, powder coatings, waterborne coatings, electrophoretic coatings, and radiation-curable coatings have emerged in succession. In the 21st century, smart coatings have risen and penetrated into various industries. Smart coatings have received extensive attention. Now the role of coatings is not limited to protection and decoration, but is gradually moving toward the direction of ecology and intelligence.

Smart coating is a new type of functional coating formed by applying smart materials or its research method to coating production. It is different from the traditional functional coating. When it is stimulated, its physicochemical properties will change along with the stimuli, and it will be responded by changes in the form, color, etc., and be expressed in an intelligent way. Intelligent coating can feel and respond to some changes in the environment in a controlled manner and in a reproducible manner, and manifest these changes in the form of changes in temperature, electric field, pressure, sound, brightness, and color. Smart coating preparation can be divided into two phases: the primary phase and the advanced phase. The former is based on nanotechnology-based smart coatings; the latter is mainly used to create smart coatings with stimulating/responsive functional films, and is regarded as a true smart coating.

The silver antibacterial application can be traced back to the BC, when people knew that silver could accelerate wound healing, prevent infections, purify water and preserve freshness. Preserving food with silverware can prevent bacteria from growing and prolong food storage. The silver element has a so-called microdynamic effect, requiring only a very small amount of silver ions to kill microorganisms such as bacteria, mold, spores, and fungi. As the size of the silver particles becomes smaller, the number of atoms on the surface of the particles increases significantly, even more than the number of atoms inside the particles, thus the silver particles exhibit a series of excellent properties different from that of bulk silver, and has been widely used in the fields of conductive paste, sterilization, catalysis, and the like. Nano-silver is adsorbed in the modified mesoporous nano-particles with the property of intelligent "on-off" and dispersed in the coating, so that the "on-off" release of nano-silver can achieve the "on-off" control of the antibacterial performance of the coating.

SUMMARY OF THE INVENTION

The present invention aims at developing a temperature-sensitive nano-silver controlled release antibacterial coating composite and a preparation method thereof to overcome the disadvantages of the low silver utilization rate and the low antibacterial efficiency of the prior silver antibacterial coating.

Thus, what is disclosed here is a temperature-sensitive nano-silver controlled release antibacterial coating composite comprising:
25~35 parts by weight of water,
30~40 parts by weight of acrylic,
20~30 parts by weight of polyurethane resin,
2~3 parts by weight of temperature-sensitive nano-silver controlled release antibacterial agent,
1.5~2.5 parts by weight of dispersant,
1.0~1.5 parts by weight of curing agent,
0.8~1.0 parts by weight of defoamer,
0.5~0.8 parts by weight of filming additive, and
0.5~0.8 parts by weight of leveling agent.

The said dispersant is selected from a carboxylate copolymer dispersant;
the said curing agent is selected from a polyamide curing agent;
the said defoamer is selected from a silicone defoamer;
the said filming additive is selected from a alcohol ether filming additive;
the said leveling agent is selected from a polysiloxane leveling agent.

The said temperature-sensitive nano-silver controlled release antibacterial agent is prepared by nanometer mesoporous $SiO_2$ modified by poly N-isopropyl acrylamide adsorbing nano silver.

Also disclosed herein is a process for preparing a temperature-sensitive nano-silver controlled release antibacterial agent, comprising the steps of:

Step 1: mixing anhydrous ethanol, ether, ammonia and deionized water at room temperature to form a first mixture, then adding cetyl trimethyl ammonium bromide to the first mixture, and stirring for 30 minutes to obtain a second mixture, then adding TEOS to the second mixture, and stirring for 48 hours to obtain a third mixture, centrifuging and filtering the third mixture to obtain a first solid powder, ultrasonically dispersing the first solid powder in deionized water to obtain a mesoporous $SiO_2$ dispersion;

Step 2: adding 3-(trimethoxysilyl)propyl methacrylate to the mesoporous $SiO_2$ dispersion, and stirring for 48 hours at room temperature to obtain a fourth mixture, then centrifuging and filtering the fourth mixture to obtain a second solid powder, ultrasonically dispersing the second solid powder in deionized water to obtain a dispersion, then adding N-isopropyl acrylamide, N, N-methylenebisacrylamide and KPS to the dispersion, reacting for 4 hours at a temperature of 70 IC to obtain a nanometer mesoporous SiO$_2$ modified by poly N-isopropyl acrylamide dispersion;

Step 3: Dissolving dioctyl sodium sulfosuccinate in dodecane to obtain a first solution, taking two equal volumes of the first solution, marking them as A and B respectively, and then stirring A and B at a high agitation speed, dropping AgNO$_3$ solution to A and stirring for 30 minutes to obtain a first transparent emulsion, and dropping equal volume of hydrazine hydrate solution to B and stirring for 30 minutes to obtain a second transparent emulsion, then adding the second transparent emulsion to the first transparent emulsion and stirring for 30 minutes to obtain a colloidal solution, gaining nano silver particles from the colloidal solution by copper mesh, and then drying the nano silver particles for 30 minutes in a vacuum at room temperature; adding the nano silver particles to the nanometer mesoporous SiO$_2$ modified by poly N-isopropyl acrylamide dispersion and then stirring for 36 hours at a high agitation speed to obtain a temperature-sensitive nano-silver controlled release antibacterial agent.

Also disclosed herein is a process for preparing a temperature-sensitive nano-silver controlled release antibacterial coating composite, comprising the steps of:

Step 1: mixing water, acrylic, polyurethane resin, dispersant, curing agent, defoamer, filming additive and leveling agent to obtain a fifth mixture;

Step 2: adding temperature-sensitive nano-silver controlled release antibacterial agent to the fifth mixture, mixing evenly with mechanical shear to obtain a temperature-sensitive nano-silver controlled release antibacterial coating composite.

Also disclosed herein is the mechanism of the said temperature-sensitive nano-silver controlled release antibacterial coating composite. Nano-silver particles of the said temperature-sensitive nano-silver controlled release antibacterial agent is adsorbed in the mesopores of nano-mesoporous SiO$_2$ modified by poly N-isopropyl acrylamide (PNIPAM), because PNIPAM has a phase transition temperature (about 32° C.), making it has a temperature stimulus/response characteristic. Above 32° C., PNIPAM on the surface of nano-mesoporous SiO$_2$ particles will shrink, blocking the mesopores and thus preventing the release of internal nano-Ag. When the temperature is below 32° C., PNIPAM on the surface of nano-mesoporous SiO$_2$ particles will be in the dilated state, the release of internal nano-Ag becomes unimpeded, so that controlled release of nano Ag can be achieved.

The present invention offers the following significant advantages:

1) The temperature-sensitive nano-silver controlled release antibacterial coating composite prepared by the invention has excellent antibacterial performance, and does not contain formaldehyde, mercury and other heavy metals, and has no toxicity, no pollution, good water resistance, good weather resistance and strong adhesion. The nano silver powder absorbed in the nano mesoporous material does not settle down, so the coating will not change color. Stored the prepared coating composite at room temperature for 30 days, the paint was milky white; stored the prepared coating composite at a temperature of 50° C. for 30 days, the coating did not discolor.

2) The smart coating prepared by this invention can be appropriately "on-off" controlled of its antibacterial properties according to actual needs. Through the control of temperature, the release of nano-silver in the mesoporous nano-SiO$_2$ of the coating film layer is controlled. It's not only to protect the nano-silver, but also to control the strength of the anti-bacterial properties according to actual needs and improve the use efficiency of nano silver particles. This invention is in line with the new concept of "Intelligent Age" in the 21st century.

The present invention is further described with the drawings as follows.

DESCRIPTION OF THE PREFERRED EMBODIMENTS

Figure 1:
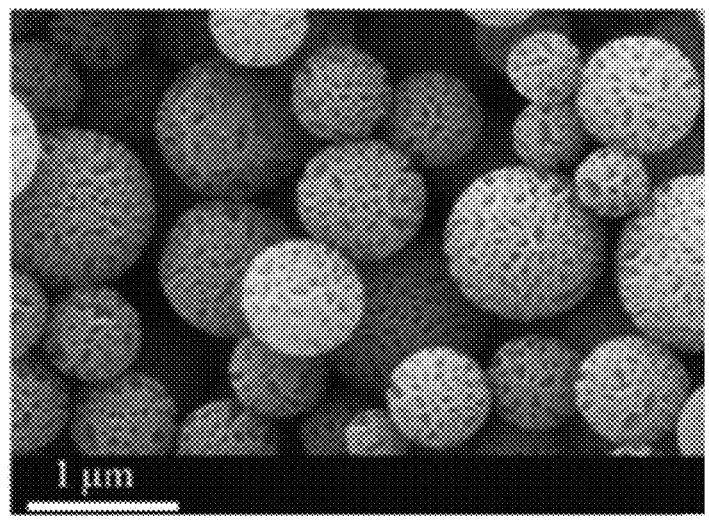
FIG. 1 is a SEM image of mesoporous nanosilica in one embodiment of the present invention.
Figure 2:
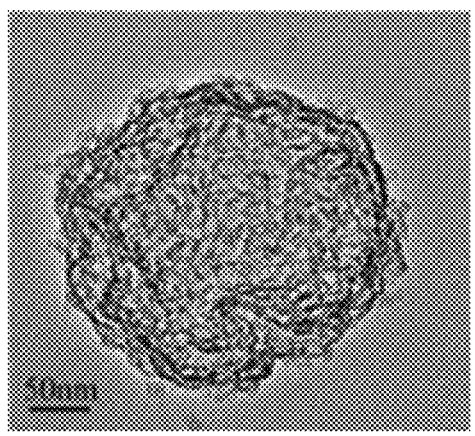
FIG. 2 is a TEM image of nanoporous mesoporous silica after adsorption of nanosilver in one embodiment of the present invention.

The present invention is further described in the following exemplified embodiments to illustrate the application of the principles of the invention. It is understood that the invention may be embodied otherwise without departing from such principles. The scope of the claims of the present invention expressly should not be limited to such exemplary or preferred embodiments.

Embodiment 1

A temperature-sensitive nano-silver controlled release antibacterial coating composite comprises:

25 parts by weight of water,
30 parts by weight of acrylic,
20 parts by weight of polyurethane resin,
2 parts by weight of temperature-sensitive nano-silver controlled release antibacterial agent,
1.5 parts by weight of dispersant,
1.0 parts by weight of curing agent,
0.8 parts by weight of defoamer,
0.5 parts by weight of filming additive, and
0.5 parts by weight of leveling agent.

The said temperature-sensitive nano-silver controlled release antibacterial agent is prepared by a process comprising the steps of:

Step 1: mixing 60 mL anhydrous ethanol, 10 mL ether, 5 mL ammonia and 9 mL deionized water at room temperature to form a first mixture, then adding 1 g cetyl trimethyl ammonium bromide to the first mixture, and stirring for 30 minutes to obtain a second mixture, then adding 4.5 mL TEOS to the second mixture, and stirring for 48 hours to obtain a third mixture, centrifuging and filtering the third mixture to obtain a first solid powder, ultrasonically dispersing the first solid powder in deionized water to obtain a mesoporous SiO$_2$ dispersion;

Step 2: adding 3 mL 3-(trimethoxysilyl)propyl methacrylate to the mesoporous SiO$_2$ dispersion, and stirring for 48 hours at room temperature to obtain a fourth mixture, then centrifuging and filtering the fourth mixture to obtain a second solid powder, ultrasonically dispersing the second solid powder in 150 mL deionized water to obtain a dispersion, then adding 1.5 g N-isopropyl acrylamide, 0.15 g N,N-methylenebisacrylamide and 0.03 g KPS to the dispersion, reacting for 4 hours at a temperature of 70° C. to obtain a nanometer mesoporous SiO$_2$ modified by poly N-isopropyl acrylamide dispersion;

Step 3: Dissolving dioctyl sodium sulfosuccinate in dodecane to obtain a first solution with the concentrate of 0.1 mol/L, taking two 20 mL of the first solution, marking them as A and B respectively, and then stirring A and B at a high agitation speed, dropping 20 mL 0.1 mol/L AgNO$_3$ solution to A and stirring for 30 minutes to obtain a first transparent emulsion, and dropping 20 mL 0.2 mol/L hydrazine hydrate solution to B and stirring for 30 minutes to obtain a second transparent emulsion, then adding the second transparent emulsion to the first transparent emulsion and stirring for 30 minutes to obtain a colloidal solution, gaining nano silver particles from the colloidal solution by copper mesh, and then drying the nano silver particles for 30 minutes in a vacuum at room temperature; adding the nano silver particles to the nanometer mesoporous $SiO_2$ modified by poly N-isopropyl acrylamide dispersion and then stirring for 36 hours at a high agitation speed to obtain a temperature-sensitive nano-silver controlled release antibacterial agent.

A process for preparing a temperature-sensitive nano-silver controlled release antibacterial coating composite comprises the steps of:

Step 1: mixing water, acrylic, polyurethane resin, dispersant, curing agent, defoamer, filming additive and leveling agent to obtain a fifth mixture;

Step 2: adding temperature-sensitive nano-silver controlled release antibacterial agent to the fifth mixture, mixing evenly with mechanical shear to obtain a temperature-sensitive nano-silver controlled release antibacterial coating composite.

Embodiment 2

A temperature-sensitive nano-silver controlled release antibacterial coating composite comprises:
35 parts by weight of water,
40 parts by weight of acrylic.
30 parts by weight of polyurethane resin,
3 parts by weight of temperature-sensitive nano-silver controlled release antibacterial agent,
2.5 parts by weight of dispersant,
1.5 parts by weight of curing agent,
1.0 parts by weight of defoamer,
0.8 parts by weight of filming additive, and
0.8 parts by weight of leveling agent.

The process for preparing the temperature-sensitive nano silver controlled release antimicrobial agent is the same as that of embodiment 1.

A process for preparing a temperature-sensitive nano-silver controlled release antibacterial coating composite comprises the steps of:

Step 1: mixing water, acrylic, polyurethane resin, dispersant, curing agent, defoamer, filming additive and leveling agent to obtain a fifth mixture;

Step 2: adding temperature-sensitive nano-silver controlled release antibacterial agent to the fifth mixture, mixing evenly with mechanical shear to obtain a temperature-sensitive nano-silver controlled release antibacterial coating composite.

Embodiment 3

A temperature-sensitive nano-silver controlled release antibacterial coating composite comprises:
30 parts by weight of water,
35 parts by weight of acrylic,
25 parts by weight of polyurethane resin,
2.5 parts by weight of temperature-sensitive nano-silver controlled release antibacterial agent,
2 parts by weight of dispersant,
1.2 parts by weight of curing agent,
0.9 parts by weight of defoamer,
0.7 parts by weight of filming additive, and
0.6 parts by weight of leveling agent.

The process for preparing the temperature-sensitive nano silver controlled release antimicrobial agent is the same as that of embodiment 1.

A process for preparing a temperature-sensitive nano-silver controlled release antibacterial coating composite comprises the steps of:

Step 1: mixing water, acrylic, polyurethane resin, dispersant, curing agent, defoamer, filming additive and leveling agent to obtain a fifth mixture;

Step 2: adding temperature-sensitive nano-silver controlled release antibacterial agent to the fifth mixture, mixing evenly with mechanical shear to obtain a temperature-sensitive nano-silver controlled release antibacterial coating composite.

Embodiment 4

A nano-silver antibacterial coating composite comprises:
25 parts by weight of water.
30 parts by weight of acrylic,
20 parts by weight of polyurethane resin,
2 parts by weight of nano-silver antibacterial agent,
1.5 parts by weight of dispersant,
1.0 parts by weight of curing agent,
0.8 parts by weight of defoamer.
0.5 parts by weight of filming additive, and
0.5 parts by weight of leveling agent.

A process for preparing a nano-silver antibacterial coating composite comprises the steps of:

Step 1: mixing water, acrylic, polyurethane resin, dispersant, curing agent, defoamer, filming additive and leveling agent to obtain a fifth mixture;

Step 2: adding nano-silver antibacterial agent to the fifth mixture, mixing evenly with mechanical shear to obtain a nano-silver antibacterial coating composite.

The antibacterial ability Control data for the different coatings prepared by Embodiment 1-4 at Different temperatures are compared in Table 1:

TABLE 1

Comparison of antibacterial ability results

| Test items | Coatings prepared by Embodiment 1-3 | | Coatings prepared by Embodiment 4 | |
|---|---|---|---|---|
| | 28° C. | 40° C. | 28° C. | 40° C. |
| Anti-*Escherichia coli* kill rate after 24 hours | >98% | 30%-40% | >95% | >95% |
| Anti-*Staphylococcus aureus* killing rate after 24 hours | >98% | 30%-40% | >95% | >95% |
| Anti-*Klebsiella Pneumoniae* Killing Rate after 24 Hours | >98% | 30%-40% | >95% | >95% |
| Antibacterial persistence | 90 days | 100 days | 50 days | 40 days |

It can be seen from the antibacterial ability control data in table 1, coatings prepared by this invention can really control the antibacterial ability by controlling the temperature, the coatings' killing rate of the bacteria of the is more than 98% at 28° C., and the coatings' killing rate of the bacteria at 40° C. is adjusted to 30%-40%. However, the bacteria killing rate of the coating prepared by Embodiment 4 cannot change with the change of temperature; and the antibacterial durability of the coating of the present invention is much larger than that of the ordinary nano silver antibacterial coating.

The performance data for the coatings prepared by Embodiment 1-3 are showed in Table 2:

TABLE 2

Comparison of performance results

| Coating appearance | Level and smooth |
|---|---|
| hardness | >H |
| Adhesion | <level 2 |
| Drying time: surface dry | 40 min-50 min |
| Drying time: Completely dry | 48 h |
| Low temperature stability | No abnormality |
| Coating temperature change (5 cycles) | No abnormality |
| Alkaline resistance (48 h) | No abnormality |
| Tensile Strength/% | >1.5 MPa |
| Elongation at break/% | >230% |

What is claimed is:

1. A temperature-sensitive nano-silver controlled release antibacterial coating composite comprising:
    25~35 parts by weight of water,
    30~40 parts by weight of acrylic,
    20~30 parts by weight of polyurethane resin,
    2~3 parts by weight of temperature-sensitive nano-silver controlled release antibacterial agent,
    1.5~2.5 parts by weight of dispersant,
    1.0~1.5 parts by weight of curing agent,
    0.8~1.0 parts by weight of defoamer,
    0.5~0.8 parts by weight of filming additive, and
    0.5~0.8 parts by weight of leveling agent;
    wherein the temperature-sensitive nano-silver controlled release antibacterial agent is nano-silver adsorbed to particles of nanometer mesoporous $SiO_2$ modified by poly N-isopropyl acrylamide;
    above 32° C. poly N-isopropyl acrylamide on the surface of nano-mesoporous $SiO_2$ particles will shrink, blocking the mesopores and thus preventing the release of internal nano-Ag: when the temperature is below 32° C. poly N-isopropyl acrylamide on the surface of nano-mesoporous $SiO_2$ particles will be in the dilated state, the release of internal nano-Ag becomes unimpeded, so that controlled release of nano Ag can be achieved.

2. The composite as claimed in claim 1, wherein
    the dispersant is selected from a carboxylate copolymer dispersant;
    and the curing agent is selected from a polyamide curing agent;
    and the defoamer is selected from a silicone defoamer;
    and the filming additive is selected from a alcohol ether filming additive;
    and the leveling agent is selected from a polysiloxane leveling agent.

3. The composite as claimed in claim 1, wherein the temperature-sensitive nano-silver controlled release antibacterial agent is prepared by nanometer mesoporous $SiO_2$ modified by poly N-isopropyl acrylamide adsorbing nano silver; including the following steps:
    Step 1: mixing anhydrous ethanol, ether, ammonia and deionized water at room temperature to form a first mixture, then adding cetyl trimethyl ammonium bromide to the first mixture, and stirring for 30 minutes to obtain a second mixture, then adding TEOS to the second mixture, and stirring for 48 hours to obtain a third mixture, centrifuging and filtering the third mixture to obtain a first solid powder, ultrasonically dispersing the first solid powder in deionized water to obtain a mesoporous $SiO_2$ dispersion;
    Step 2: adding 3-(trimethoxysilyl)propyl methacrylate to the mesoporous $SiO_2$ dispersion, and stirring for 48 hours at room temperature to obtain a fourth mixture, then centrifuging and filtering the fourth mixture to obtain a second solid powder, ultrasonically dispersing the second solid powder in deionized water to obtain a dispersion, then adding N-isopropyl acrylamide, N, N-methylenebisacrylamide and KPS to the dispersion, reacting for 4 hours at a temperature of 70° C. to obtain a nanometer mesoporous $SiO_2$ modified by poly N-isopropyl acrylamide dispersion;
    Step 3: Dissolving dioctyl sodium sulfosuccinate in dodecane to obtain a first solution, taking two equal volumes of the first solution, marking them as A and B respectively, and then stirring A and B at a high agitation speed, dropping $AgNO_3$ solution to A and stirring for 30 minutes to obtain a first transparent emulsion, and dropping equal volume of hydrazine hydrate solution to B and stirring for 30 minutes to obtain a second transparent emulsion, then adding the second transparent emulsion to the first transparent emulsion and stirring for 30 minutes to obtain a colloidal solution, gaining nano silver particles from the colloidal solution by copper mesh, and then drying the nano silver particles for 30 minutes in a vacuum at room temperature; adding the nano silver particles to the nanometer mesoporous $SiO_2$ modified by poly N-isopropyl acrylamide dispersion and then stirring for 36 hours at a high agitation speed to obtain a temperature-sensitive nano-silver controlled release antibacterial agent.

4. A process for preparing a temperature-sensitive nano-silver controlled release antibacterial coating composite as claimed in claim 1, comprising the steps of:
    Step 1: mixing water, acrylic, polyurethane resin, dispersant, curing agent, defoamer, filming additive and leveling agent to obtain a fifth mixture;
    Step 2: adding temperature-sensitive nano-silver controlled release antibacterial agent to the fifth mixture, mixing evenly with mechanical shear to obtain a temperature-sensitive nano-silver controlled release antibacterial coating composite.

5. The process according to claim 4 wherein
    the dispersant is selected from a carboxylate copolymer dispersant;
    and the curing agent is selected from a polyamide curing agent;
    and the defoamer is selected from a silicone defoamer;
    and the filming additive is selected from a alcohol ether filming additive;
    and the leveling agent is selected from a polysiloxane leveling agent.

6. The process according to claim 4 wherein the temperature-sensitive nano-silver controlled release antibacterial agent is prepared by nanometer mesoporous $SiO_2$ modified by poly N-isopropyl acrylamide adsorbing nano silver; including the following steps:
    Step 1: mixing anhydrous ethanol, ether, ammonia and deionized water at room temperature to form a first mixture, then adding cetyl trimethyl ammonium bromide to the first mixture, and stirring for 30 minutes to obtain a second mixture, then adding TEOS to the second mixture, and stirring for 48 hours to obtain a third mixture, centrifuging and filtering the third mixture to obtain a first solid powder, ultrasonically dispersing the first solid powder in deionized water to obtain a mesoporous $SiO_2$ dispersion;

Step 2: adding 3-(trimethoxysilyl)propyl methacrylate to the mesoporous $SiO_2$ dispersion, and stirring for 48 hours at room temperature to obtain a fourth mixture, then centrifuging and filtering the fourth mixture to obtain a second solid powder, ultrasonically dispersing the second solid powder in deionized water to obtain a dispersion, then adding N-isopropyl acrylamide, N,N-methylenebisacrylamide and KPS to the dispersion, reacting for 4 hours at a temperature of 70° C. to obtain a nanometer mesoporous $SiO_2$ modified by poly N-isopropyl acrylamide dispersion;

Step 3: Dissolving dioctyl sodium sulfosuccinate in dodecane to obtain a first solution, taking two equal volumes of the first solution, marking them as A and B respectively, and then stirring A and B at a high agitation speed, dropping $AgNO_3$ solution to A and stirring for 30 minutes to obtain a first transparent emulsion, and dropping equal volume of hydrazine hydrate solution to B and stirring for 30 minutes to obtain a second transparent emulsion, then adding the second transparent emulsion to the first transparent emulsion and stirring for 30 minutes to obtain a colloidal solution, gaining nano silver particles from the colloidal solution by copper mesh, and then drying the nano silver particles for 30 minutes in a vacuum at room temperature; adding the nano silver particles to the nanometer mesoporous $SiO_2$ modified by poly N-isopropyl acrylamide dispersion and then stirring for 36 hours at a high agitation speed to obtain a temperature-sensitive nano-silver controlled release antibacterial agent.

* * * * *